United States Patent
Duckett, III

(10) Patent No.: US 9,433,341 B2
(45) Date of Patent: Sep. 6, 2016

(54) COMPENSATED RELAYS FOR REDUCING NUMBER OF ELEMENTS IN ROD LENS ENDOSCOPES

(75) Inventor: George E. Duckett, III, Castaic, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 239 days.

(21) Appl. No.: 13/429,853

(22) Filed: Mar. 26, 2012

(65) Prior Publication Data
US 2013/0253273 A1   Sep. 26, 2013

(51) Int. Cl.
| | |
|---|---|
| A61B 1/06 | (2006.01) |
| A61B 1/04 | (2006.01) |
| A61B 1/00 | (2006.01) |
| A61B 1/002 | (2006.01) |
| G02B 23/24 | (2006.01) |
| H04N 5/225 | (2006.01) |
| A61B 1/055 | (2006.01) |
| A61B 1/07 | (2006.01) |
| G02B 13/00 | (2006.01) |

(52) U.S. Cl.
CPC ........... *A61B 1/002* (2013.01); *G02B 23/2446* (2013.01); *A61B 1/00096* (2013.01); *A61B 1/00163* (2013.01); *A61B 1/055* (2013.01); *A61B 1/07* (2013.01); *G02B 13/0095* (2013.01); *H04N 5/225* (2013.01); *H04N 2005/2255* (2013.01)

(58) Field of Classification Search
CPC .. A61B 1/055; A61B 1/00163; A61B 1/002; A61B 1/00096; A61B 1/07; G02B 13/004
USPC ........ 600/128, 130, 138, 167, 168; 362/574; 359/434, 435, 754, 772
See application file for complete search history.

(56) References Cited

U.S. PATENT DOCUMENTS

| | | | | |
|---|---|---|---|---|
| 3,561,432 A | * | 2/1971 | Yamaki et al. | 600/167 |
| 4,693,568 A | | 9/1987 | Takahashi | |
| 4,755,029 A | * | 7/1988 | Okabe | 359/654 |
| 4,988,172 A | | 1/1991 | Kanamori et al. | |
| 4,993,817 A | | 2/1991 | Hoogland | |
| 5,005,957 A | * | 4/1991 | Kanamori et al. | 359/708 |
| 5,059,009 A | * | 10/1991 | McKinley | 359/435 |
| 5,142,410 A | | 8/1992 | Ono et al. | |
| 5,361,166 A | | 11/1994 | Atkinson et al. | |
| 5,666,222 A | * | 9/1997 | Ning | 359/435 |
| 5,892,630 A | * | 4/1999 | Broome | 359/834 |
| 5,933,275 A | | 8/1999 | Igarashi | |
| 6,163,401 A | | 12/2000 | Igarashi | |

(Continued)

FOREIGN PATENT DOCUMENTS

WO    0163334 A1    8/2001

OTHER PUBLICATIONS

European Search Report Application No. EP 13 16 0984 Completed: Jul. 15, 2013; Mailing Date: Jul. 25, 2013 10 pages.
Stone, et al.; "Hybrid Diffractive-Refractive Lenses and Achromats"; Applied Optics/vol. 27, No. 14/ Jul. 15, 1988; pp. 2960-2971.
EP Office Action Application No. 13160984.4 Mailed: Nov. 4, 2015 Completed Nov. 4, 2015 6 Pages.

*Primary Examiner* — John P Leubecker
*Assistant Examiner* — William Chou
(74) *Attorney, Agent, or Firm* — Whitmyer IP Group LLC

(57) ABSTRACT

An endoscope and optical system for an endoscope having rod lenses and correction lens groups where the number of relay lens systems is greater than the number of correction lens groups in the endoscope and optical system of the endoscope.

20 Claims, 7 Drawing Sheets

(56) References Cited

U.S. PATENT DOCUMENTS

| | | |
|---|---|---|
| 7,515,335 B2 | 4/2009 | Tomioka |
| 7,724,430 B2 | 5/2010 | Kasai |
| 2002/0057501 A1* | 5/2002 | Lei .................................. 359/645 |
| 2005/0119529 A1* | 6/2005 | Farr et al. ...................... 600/160 |
| 2008/0273247 A1* | 11/2008 | Kazakevich ................... 359/637 |
| 2009/0054791 A1* | 2/2009 | Flusberg ............... A61B 5/0059 600/478 |
| 2010/0014161 A1* | 1/2010 | Kasai ........................... 359/434 |
| 2011/0285995 A1* | 11/2011 | Tkaczyk et al. .............. 356/326 |

\* cited by examiner

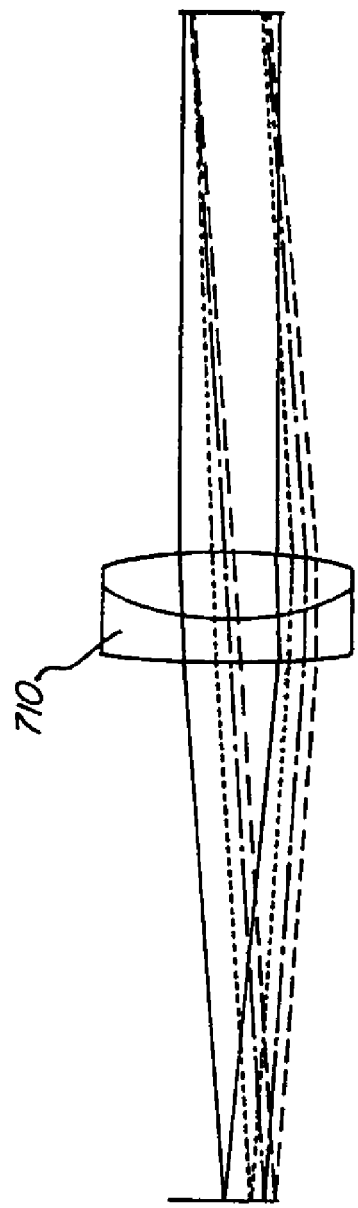
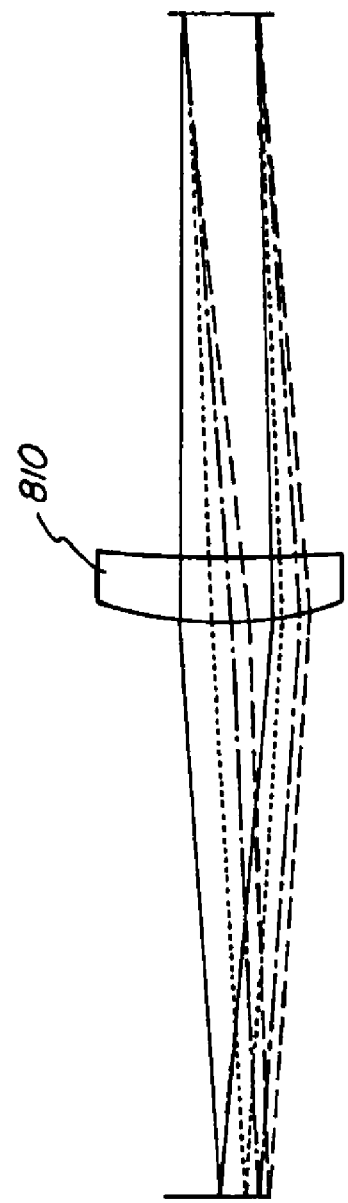

COMPENSATED RELAYS FOR REDUCING NUMBER OF ELEMENTS IN ROD LENS ENDOSCOPES

FIELD OF THE INVENTION

The invention is directed to reducing the number of optical elements in a rod lens endoscope.

BACKGROUND OF THE INVENTION

The use of optical elements in rod lens endoscopes is well known. Rod lens endoscopes typically include two identical rod lenses in their rod lens system and combine the rod lenses symmetrically to relay the image from the objective at a magnification of −1.

A series of these relay pairs convey an image from the objective to an internal image plane. For a right side up image when viewed with an eyepiece, the image is relayed an odd number of times. Therefore, the number of rod lenses in a rod lens system is calculated by using the equation 2+4n where n is an integer (e.g., 2, 6, 10, 14, etc.).

In symmetric rod lens systems, coma, distortion, and lateral color are automatically corrected for each relay pair. Spherical aberration and axial chromatic aberration are corrected by design of the rod lens systems. Astigmatism and field curvature, however, are not corrected, and accumulate with each additional relay. They are generally compensated for in the objective.

To correct for axial chromatic aberration and spherical aberration, each rod lens must have at least two components. Each rod lens is typically a doublet or a triplet. A doublet is a type of lens made up of two simple lenses paired together. A triplet is a type of lens made up of three simple lenses paired together.

Prior art systems require that the rod lenses are doublets to work and that there is at least one correction element or correction lens group in each relay lens system, thus having multiple correction lens groups through the entire optical system. For example, U.S. Pat. No. 7,724,430 to Kasai discloses a rigid endoscope and image transfer optical system having relay lens systems (Re1 to Re7) each having a correction lens group in each of the relay lens systems. Each of Re1 to Re 7 has a triplet positive lens located between each of the rod lenses in the relay lens system. U.S. Pat. No. 7,515,335 to Tomioka discloses endoscope relay lens for a rigid endoscope where the inner end of the lens unit is a cemented doublet, thus having two cemented doublets per relay lens system.

U.S. Pat. Nos. 5,933,275 and 6,163,401 to Igarashi disclose an optical system for non-flexible endoscopes having a plurality of relay lens units, the relay lens units having two bioconvex cemented doublets. U.S. Pat. No. 4,993,817 to Hoogland discloses an endoscope relay optics design having a pair of doublet lens assemblies for incorporation into an optical transfer system. U.S. Pat. No. 4,988,172 to Kanamori et al. discloses an optical system for endoscopes having a relay lens having an achromatic doublet lens consisting of a common glass lens. U.S. Pat. No. 4,693,568 to Takahashi discloses an image transmission optical system for an endoscope comprising two rod-like biconvex lenses and two thick meniscus lenses arranged between the two rod-like biconvex lenses. All of these prior art references disclose a high number of optical elements in each relay lens system. It is disadvantageous to have a high number of optical elements in each relay lens system.

Thus, it is desirable to decrease the number of optical elements in each relay lens system and also to decrease the number of optical elements in the overall endoscope as a whole. Decreasing the number of optical elements reduces the overall cost of the optical system because each additional lens has a cost and decreasing the overall number of optical elements in the system decreases the cost of the system.

Thus, it is desirable to provide an optical system where the spherical aberration and axial chromatic aberration in the entire series of rod lenses is corrected by a doublet or a triplet located between the rod lenses in one or more of the relays, but not in each relay lens system. This allows for the number of optical elements to be reduced, while still allowing for the axial chromatic aberration and spherical aberration to be corrected.

SUMMARY OF THE INVENTION

The present invention, thus, discloses a novel, unique and improved relay lens for an endoscope or an instrument. The present invention provides for an improved rod lens system that reduces the number of optical elements (and therefore cost) in a rod lens endoscope system.

Objects of the invention are achieved by providing an endoscope comprising: a shaft comprising a proximal end and a distal end and a longitudinal axis spanning the proximal end and the distal end; an optical system disposed in the shaft, the optical system including an objective lens system, and a first relay lens system, the first relay lens system having at least two rod lenses arranged in a series, and a correction lens group located between the at least two rod lenses; and at least one additional relay lens system, the at least one additional relay lens system arranged in series with the first relay lens system, such that the number of additional relay lens systems is greater than the number of relay lens systems that have a correction lens group.

The first relay lens system may be located in various locations in the relay lens system, such as being located between any of the additional relay lens system in the series. The first relay lens system may be located between an additional relay lens system and the objective lens system. The first relay lens system may be located between an additional relay lens system and the ocular lens.

As defined above, the correction lens group can include one or more lenses or lens elements.

In certain embodiments, the at least one additional relay lens system does not have a correction lens group.

In certain embodiments, the entire optical system has a single correction lens group, the single correction lens group located in the first relay lens system. In this embodiment, the single correction lens group corrects the spherical aberration and axial chromatic aberration in the entire rod lens system.

In certain embodiments, the number of relay lens systems is greater than the number of correction lens groups in the entire optical system.

In certain embodiments, the first relay lens system is located between a second relay lens system and a third relay lens system. In certain embodiments, the first relay lens system is located on either end of the series of relay lens systems, such as being located next to the objective lens system or an ocular lens. In certain embodiments, the first relay lens system is located between a second relay lens system and the objective.

In certain embodiments, the endoscope has an ocular lens. In certain embodiments, the first relay lens system is located between a second relay lens system and the ocular lens.

In certain embodiments, the at least two rod lenses of the first relay lens system are singlets.

In certain embodiments, the correction lens group in the first relay lens system is a singlet, a doublet or a triplet. In certain embodiments, the correction lens group is a diffractive/refractive hybrid singlet.

Other objects of the invention are achieved by providing an optical system for an endoscope comprising: a first relay lens system, the first relay lens system having at least two rod lenses arranged in a series, and a correction lens group, the correction lens group located between the at least two rod lenses; and at least one additional relay lens system, the at least one additional relay lens system having at least two rod lenses arranged in a series, so that the number of additional relay lens systems is greater than the number of relay lens systems that have correction lens groups. As defined above, the correction lens group can include one or more lenses or lens elements.

In certain embodiments, the correction lens group corrects aberration of the relay lens system and the objective lens system. The aberration may be spherical aberration, axial chromatic aberration and any other types of known aberrations in the art.

In certain embodiments, the correction lens group corrects aberration of an ocular lens. The ocular lens may be connected in series with the optical system, i.e., the ocular lens may be connected in series with the first relay lens system and the additional relay lens systems.

In certain embodiments, the correction lens group is a singlet, a doublet, or a triplet.

In certain embodiments, the correction lens group does not contribute to distortion, lateral chromatic aberration, astigmatism or field curvature.

In certain embodiments, the first relay lens system is located between a second relay lens system and a third relay lens system. In certain embodiments, the first relay lens system is located on either end of the series of relay lens systems.

Other objects of the invention are achieved by providing two or more relay lens systems for an optical system of an endoscope comprising: a first relay lens system comprising at least two rod lenses arranged in a series, and a correction lens group, the correction lens group located between the at least two rod lenses; and at least one additional relay lens system, the at least one additional relay lens system each having at least two rod lenses arranged in a series, so that the number of additional relay lens systems is greater than the number of relay lens systems that have a correction lens group.

In certain embodiments, the first relay lens system is located between a second relay lens system and a third relay lens system. In certain embodiments, the first relay lens system is located on either end of the series of relay lens systems.

In certain embodiments, the first rod lens and the second rod lens are a singlet. In certain embodiments, the singlet is a diffractive/refractive hybrid singlet.

In certain embodiments, the correction lens group corrects spherical aberration of the two or more relay lens systems. In certain embodiments, the correction lens group corrects axial chromatic aberration of the two or more relay lens systems. The correction lens group may also correct other types of aberrations known in the art.

In certain embodiments, the at least one additional relay lens system does not have a correction lens group.

In certain embodiments, the number of relay lens systems is greater than the number of correction lens groups in the optical system.

Other objects of the invention are achieved by providing various methods of assembly and manufacture of an endoscope with a relay lens system that has a correction lens group located between at least two rod lenses.

This includes providing a method for assembling a relay lens system comprising: providing a first relay lens system, the first relay lens system having at least two rod lenses arranged in a series; providing a correction lens group; locating the correction lens group between the at least two rod lenses of the first relay lens system; providing at least one additional relay lens system; arranging the at least one additional relay lens system in series with the first relay lens system, such that the number of additional relay lens systems is greater than the number of relay lens systems that have a correction lens group.

Other steps include providing an objective lens system and an ocular lens in series with the first relay lens system to form the optical system and disposing the optical system in a shaft of an endoscope.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 7 is a standard ocular of the prior art;

FIG. 8 is an ocular of an embodiment of the present invention;

DETAILED DESCRIPTION OF THE INVENTION

Figure 1:
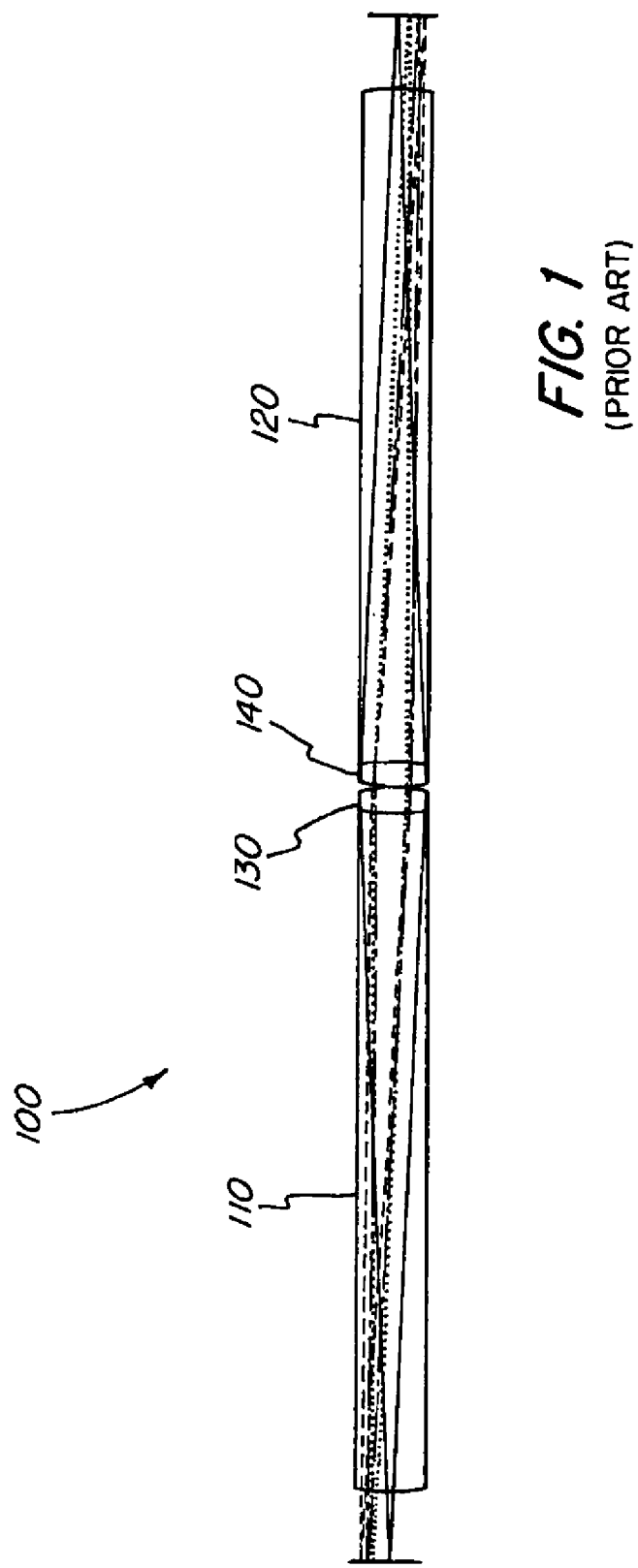
FIG. 1 is a standard rod lens relay of the prior art.

The present invention is directed to a novel, unique and improved relay lens for an endoscope or instrument that reduces the number of optical elements (and therefore cost) in rod lens endoscope system. The present invention, while reducing the number of optical elements, produces a performance equivalent to that of a conventional rod lens endoscope.

The invention is directed to a novel design that is an alternative to correcting the spherical aberration and axial chromatic aberration in each relay lens system. Instead, all of the spherical aberration and axial chromatic aberration of the entire series of rod lenses is corrected by one or more lenses located between the two rod lenses of one or more of the relay lens systems. These one or more lenses are referred to herein as a correction lens group. The correction lens group allows each of the rod lenses to be made singlets instead of doublets. In certain embodiments, there is a fewer number of the correction lens groups than the number of relay lens systems, the total element count is reduced.

In certain embodiments, the correction lens group may compensate for aberrations in the objective and/or ocular to further reduce element count. The region between the rod lenses, where the beam is collimated, provides an ideal location for the correction lens group. Since the correction lens group is made of one or more thin lenses at the aperture stop, the correction lens group does not contribute to distortion or lateral chromatic aberration. The power is negligible, so the correction lens group does not contribute to astigmatism or field curvature. Thus there are sufficient degrees of freedom to correct coma, as well as set spherical aberration and axial chromatic aberration to arbitrary values limited only by the constraints of available materials without affecting the other aberrations.

In embodiments of the invention, one or more thin doublets or triplets are incorporated into the relay portion (relay lens system) of an endoscope. These elements are used to correct the spherical aberration and axial chromatic aberration of the relay system. In certain embodiments, a correction lens group corrects all of the axial chromatic and spherical aberration. The correction lens group can be used to compensate for aberrations in the entire endoscope (including the objective and ocular), further reducing total element count in the optical system.

In some embodiments, an optical system may have a first relay lens system, second relay lens system and third relay lens system. The first relay lens system, second relay lens system and third relay lens system may be arranged in series where only one corrective lens group is used throughout these three relay lens systems and in the entire optical system. In some embodiments, the optical system may be incorporated within an endoscope, preferably the distal end of an endoscope shaft. In some embodiments, only one corrective lens group is used in the entire optical system and each of the rod lenses in each of the relay lens system are singlets. In some embodiments, the singlets can be a diffractive/refractive hybrid singlet.

In certain embodiments, a doublet or one or more doublets is used as correction lens group. The doublet or one or more doublets has two basic purposes: (1) to correct all of the axial chromatic aberration of the objective and the relay lenses, or of the entire endoscope (including the ocular); and (2) to correct the spherical aberration of the rod lenses, allowing the rod lenses to be singlets.

In certain embodiments of the invention, the rod lenses may have the same form as standard rod lenses, however extra axial chromatic aberration is added to the rod lenses to reduce the element count and reduce the number of doublets or completely eliminate them from the objective and/or the ocular.

FIG. 1 shows a prior art standard rod lens relay lens system 100 having lens 130 and 140 incorporated between rod lens 110 and rod lens 120.

Figure 2:
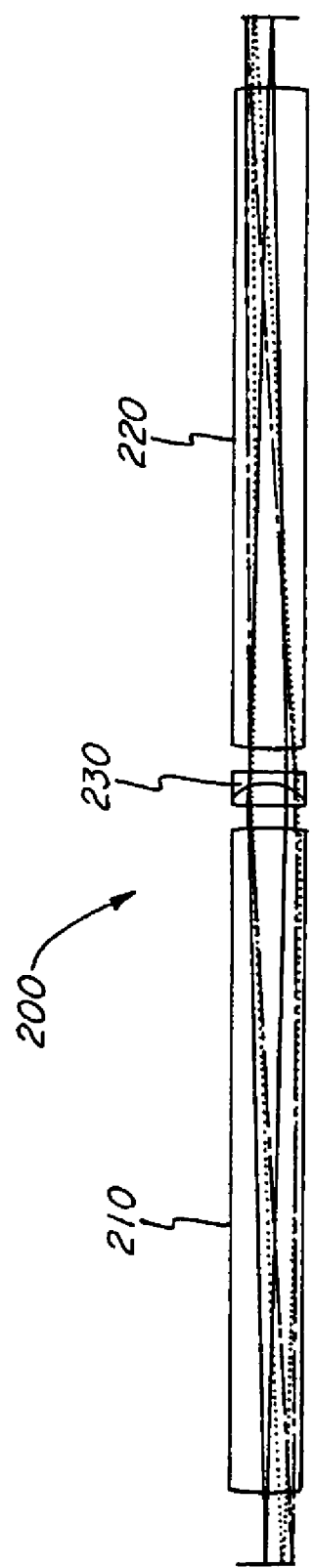
FIG. 2 is a relay with thin doublet of an embodiment of the invention.

FIG. 2 shows an improved relay lens system 200 having a thin doublet 230 incorporated between rod lens 210 and rod lens 220. This improved design allows for a reduction in the amount of lenses than known in the prior art, thus, reducing costs of production of the optical systems of endoscopes. In some embodiments, a singlet lens or a triplet may be substituted for the doublet lens 230. The single lens may be a diffractive/refractive hybrid. In other embodiments, the doublet 230 may be composed of two individual lenses and cemented together. This doublet may be shaped so that the chromatic aberration of one individual lens is counterbalanced by that of the other. In certain embodiments, having doublet lens 230 allows rod lens 210 and rod lens 220 to be singlets.

Figure 3:
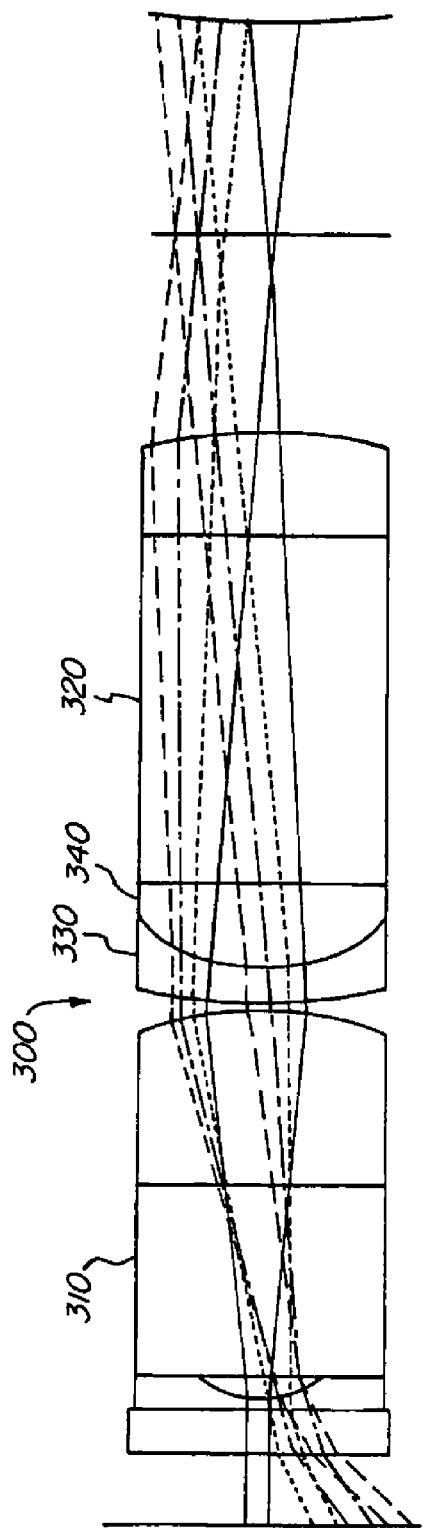
FIG. 3 is a standard objective lens of the prior art.

FIG. 3 shows a standard objective lens 300 of the prior art. Here, lenses 330 and 340 are shown between lens 310 and 320. This is in contrast to FIG. 4, which shows an objective lens 400 of an embodiment of the present invention.

Figure 4:
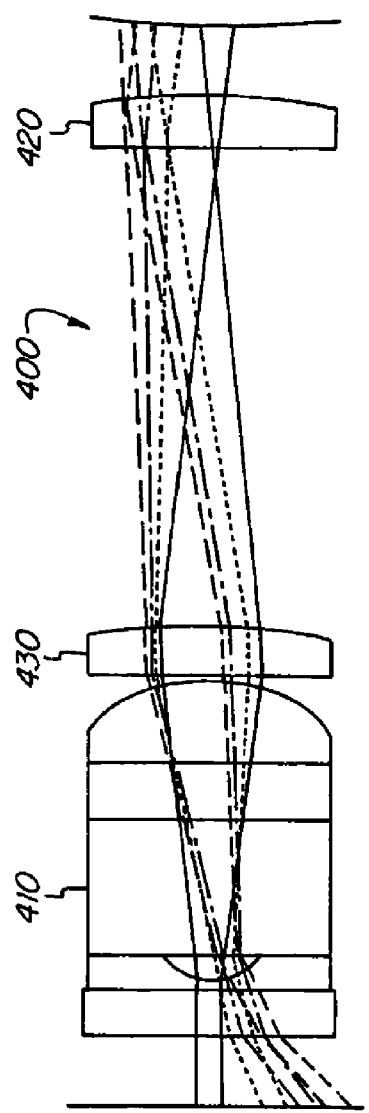
FIG. 4 is an objective lens of an embodiment of the present invention.

FIG. 4 shows an objective lens of an embodiment of the invention. Here, singlet lens 430 is shown adjacent to and touching lens 410. On the other side of singlet lens 430 is singlet lens 420.

FIG. 4 shows the result of testing an inventive 4 mm endoscope of an embodiment of the invention having six rod lenses. This design incorporated a single doublet between the third and fourth rod lenses. The objective contained no doublets, nor did the ocular.

Table 1 shows a reduction of the number of lens surfaces and curved lens surfaces of the objective lens of the present invention compared to the number of lens surfaces and curved lens surfaces of a standard objective lens in the prior art.

TABLE 1

Example Compensated Relays

| | Conventional Endoscope with a standard objective lens and relay lens system | Tested Endoscope with compensated relay lens system |
|---|---|---|
| Number of lens surfaces | 42 | 28 |
| Number of curved lens surfaces | 34 | 22 |

Figure 5:
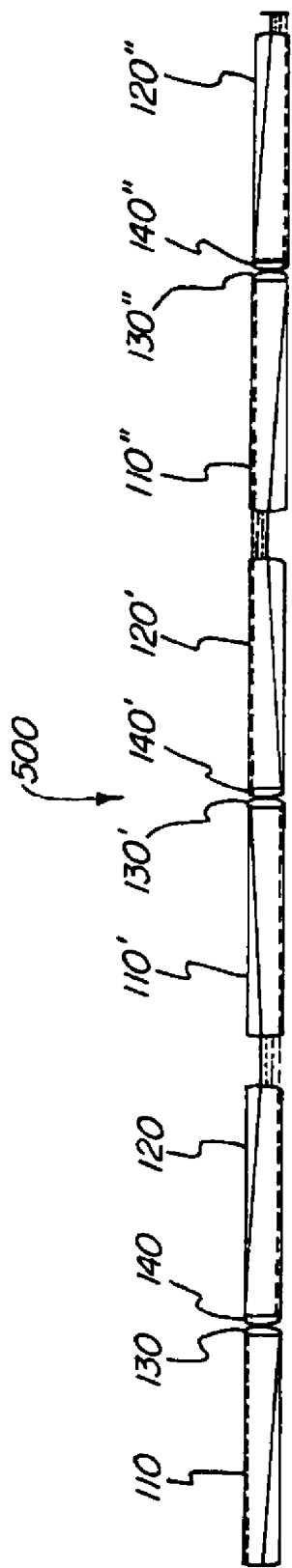
FIG. 5 is a series of relay lens systems of the prior art.
Figure 6:
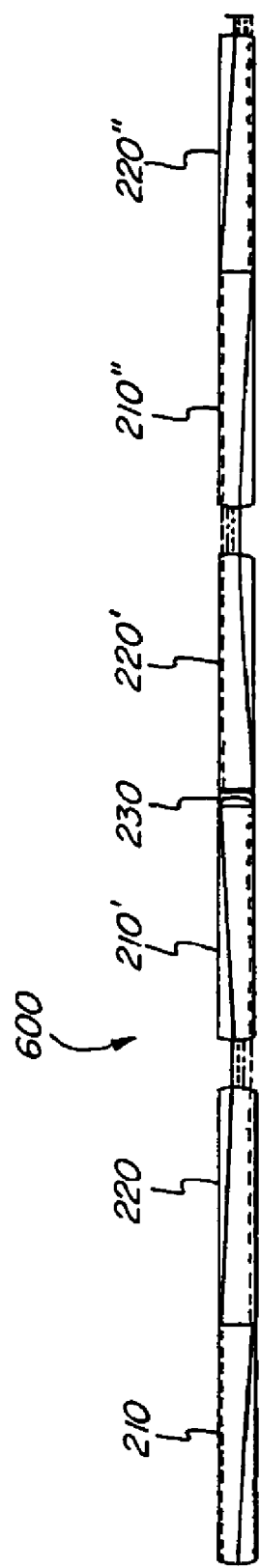
FIG. 6 is a series of relay lens system of an embodiment of the present invention.

Results in Table 1 show that the compensated relay invention with the objective as shown in FIG. 4 combined with the relay lens system of FIG. 6 produces comparable performance to a conventional 4 mm endoscope with an objective of FIG. 3 and relays of FIG. 5. The compensated relay invention has 33% fewer polished lens surfaces than the conventional 4 mm endoscope.

FIG. 5 is a series 500 of relay lens systems of the prior art having two rod lens doublets incorporated in each relay series. Here, lens 130 and lens 140 are shown between rod lens 110 and rod lens 120. Lens 130' and lens 140' are shown between rod lens 110' and rod lens 120'. Lens 130" and lens 140" are shown between rod lens 110" and rod lens 120".

In contrast to FIG. 5, FIG. 6 is a series 600 of relay lens systems of an embodiment of the present invention. Here, doublet lens 230 is shown in between rod lens 210' and rod lens 220'. Significantly, doublet lens 230 is the only correction lens group in the entire series of relay lens systems. Rod lenses 210 and 220 and 210" and 220" do not a have correction lens group located in between them. This reduces the total number of optical elements in the entire system. This overcomes disadvantages of the prior art where the spherical aberration and axial chromatic aberration is corrected in each relay lens system.

In certain embodiments, rod lenses 210 and 220 or rod lenses 210" and 220" may include a correction lens group in between the rod lenses; however, the total number of relay lens systems is greater than the number of relay lens systems having a correction lens group.

FIG. 7 shows an ocular of an embodiment of the present invention. In FIG. 7, ocular 710 is shown being a doublet lens. FIG. 8 is an ocular of an embodiment of the present invention. Here, ocular 810 is shown being a singlet lens.

Figure 9:
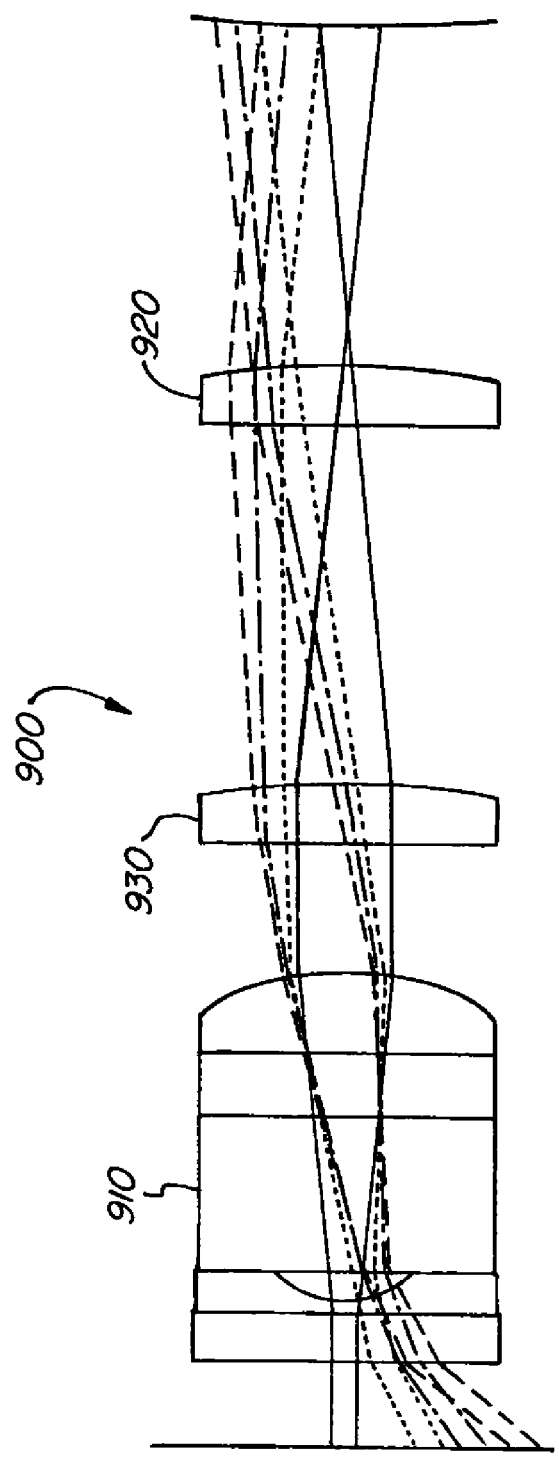
FIG. 9 is an objective lens of an embodiment of the present invention.

FIG. 9 is an objective lens of an embodiment of the present invention that is similar to FIG. 4. FIG. 9 shows an objective lens of an embodiment of the invention. Here, singlet lens 930 adjacent to lens 910. On the other side of singlet lens 930 is singlet lens 920. In FIG. 9, the appropriate overcorrected axial chromatic aberration required for each set of relays is dependent on the number of relays. This means that different compensation components may be required for a 6 rod lens system than, say, a 10 rod lens system.

Results from tests conducted show that the compensated relay invention as shown in FIG. 9 produces comparable performance to a conventional 4 mm endoscope with 14% fewer polished lens surface. Table 2, set forth below, displays results from a system that combines the objective from FIG. 9 with relays that look like regular relays but designed with extra aberration in each relay lens system:

TABLE 2

Example Compensated Relays

|  | Standard Relay Lens system | Compensated Relay Invention having relays with extra aberration in each relay |
|---|---|---|
| Number of lens surfaces | 42 | 36 |
| Number of curved lens surfaces | 34 | 30 |

In testing the invention, several relay systems incorporating correction lens groups were designed. Each correction lens group corrected for spherical aberration, coma, distortion, axial chromatic aberration, and lateral chromatic aberration. Field curvature and astigmatism are similar between the conventional relay and the analogous compensated relay.

Table 3 shows a reduction in lens surfaces of various tested designs:

TABLE 3

Example Compensated Relays

| Number of Rod Lenses | Relay Diameter [mm] | Relay Invariant [mm] | Rod Lens Glass Type | Lens Surfaces (Conventional Relay) | Compensation Elements | Lens Surfaces (Compensated Relay) | Reduction in Lens Surfaces |
|---|---|---|---|---|---|---|---|
| 6 | 2.6 | 0.079 | F2 | 24 | Doublet | 16 | 8 |
| 10 | 2.6 | 0.078 | F2 | 40 | Triplet | 26 | 14 |
| 14 | 1.2 | 0.029 | F2 | 56 | 2 Doublets (identical) | 36 | 20 |
| 10 | 2.6 | 0.076 | N-K5 | 40 | Doublet | 24 | 16 |
| 14 | 2.6 | 0.076 | N-K5 | 56 | Triplet | 34 | 22 |

Figure 10:
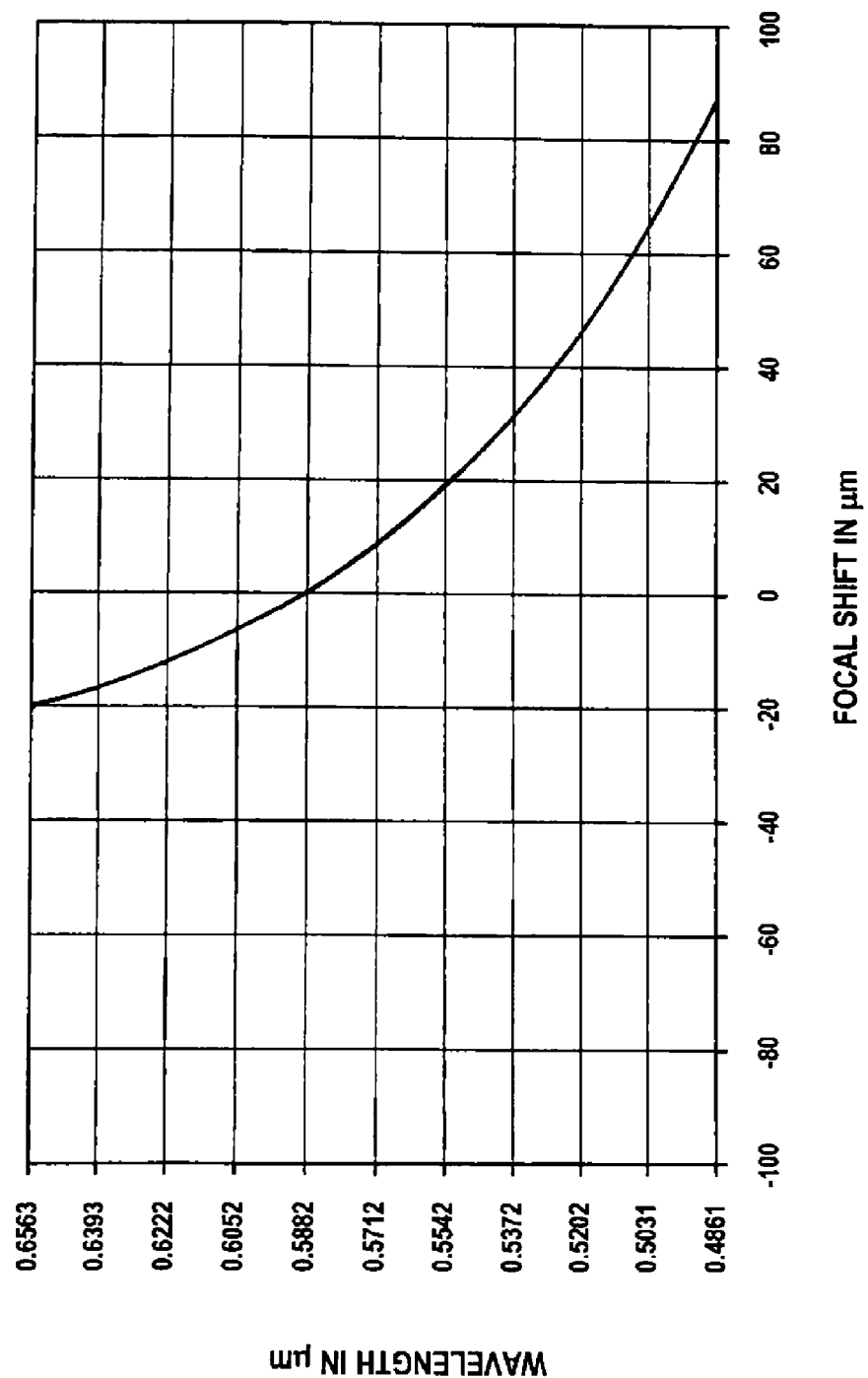
FIG. 10 is a chart showing the wavelength compared to the focal shift, showing the overcorrected axial chromatic aberration.

FIG. 10 is a chart showing the wavelength compared to the focal shift, showing the overcorrected axial chromatic aberration of the relays of the embodiments that have extra axial chromatic aberration that is added to reduce the element count or completely eliminate the number of doublets from the objective and/or the ocular. The focal shift of the aberration of tested relay designs did not vary significantly from the prior systems that incorporated a greater number of optical elements, showing that the tested designs worked just as well as the prior art design, while using fewer optical elements.

The monochromatic aberrations and the first order chromatic aberrations of the relays of the invention can be made sufficiently equal to those of the conventional relays. The limit to how much work can be extracted from the compensation elements is spherochromatism. As more and more rod lenses are added, eventually the spherochromatism becomes problematic.

There are no firm rules as to when the spherochromatism becomes problematic. Rod lenses with less dispersion (such as N-K5 vs. F2) and smaller diameter (because of scaling) have less spherochromatism, and therefore longer relays can be achieved. This is apparent in Table 3 provided above.

In certain tested embodiments, a single doublet can compensate for the aberrations in four to six rod lenses. Table 4 shows data from a conventional relay design of six traditional rod lens doublets, where aberration coefficients are provided:

TABLE 4

| Aberration coefficients for assemblage of relays of conventional relay lens system design | | |
|---|---|---|
| Spherical aberration | −0.0215246871 | W040 |
| Coma | −0.0005905055 | W131 |
| Astigmatism | 1.1625511549 | W222 |
| Field curvature | 1.6120892705 | W220 |
| Distortion | 0.0390482247 | W331 |

In a tested relay design of the invention, six rod lens singlets and a single doublet located between the first two rod lenses was tested. Table 5 shows data from a the tested system, which has aberration differences that are negligible from the conventional design in Table 4:

TABLE 5

| Aberration coefficients for assemblage of relays of the tested relay lens system design | | |
|---|---|---|
| Spherical aberration | 0.0372751140 | W040 |
| Coma | −0.0053299069 | W131 |
| Astigmatism | 1.1805529671 | W222 |

TABLE 5-continued

| Aberration coefficients for assemblage of relays of the tested relay lens system design | | |
|---|---|---|
| Field curvature | 1.6118109068 | W220 |
| Distortion | −0.0374762170 | W331 |

When using the tested system with an objective, performance was identical in the objective even through the tested system had four fewer optical elements than a conventional relay lens system.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. An endoscope comprising:
   a shaft comprising a proximal end and a distal end and a longitudinal axis spanning the proximal end and the distal end;
   an optical system disposed in the shaft, the optical system including
      an objective lens system, and
      a first relay lens system, the first relay lens system having
         at least two rod lenses arranged in a series, each of the at least two rod lenses a singlet lens, and
         one doublet correction lens located between the at least two rod lenses and no other correction lens in the first relay lens system; and
      a plurality of additional relay lens pairs each having two symmetric singlet rod lenses, the plurality of additional relay lens pairs arranged in series with the first relay lens system, such that the number of additional relay lens pairs is greater than the number of relay lens systems that have a correction lens group.

2. The endoscope of claim 1, wherein the plurality of additional relay lens pairs does not have a correction lens group.

3. The endoscope of claim 1, wherein the first relay lens system is located between a second relay lens system and a third relay lens system.

4. The endoscope of claim 1, wherein the first relay lens system is located between a second relay lens system and the objective lens system.

5. The endoscope of claim 1, further comprising an ocular lens.

6. The endoscope of claim 5, wherein the first relay lens system is located between a second relay lens system and the ocular lens.

7. The endoscope of claim 1, wherein the one doublet correction lens is cemented or uncemented.

8. The endoscope of claim 1, wherein only one correction lens group is used in the entire optical system.

9. The endoscope of claim 1, wherein the plurality of additional relay lens pairs does not have a correction lens group, and only one correction lens group is used in the entire optical system to correct aberration of the plurality of additional relay lens pairs.

10. An optical system for an endoscope comprising:
    a first relay lens system, the first relay lens system having
       at least two rod lenses arranged in a series, each of the at least two rod lenses a singlet lens, and
       one doublet correction lens located between the at least two rod lenses and no other correction lens in the first relay lens system; and
    a plurality of additional relay lens pairs each having two symmetric singlet rod lenses arranged in a series and no correction lens group, so that the number of additional relay lens pairs is greater than the number of relay lens systems that have a correction lens group.

11. The optical system of claim 10, wherein the correction lens corrects aberration of the relay lens system and an objective lens system.

12. The optical system of claim 10, wherein the correction lens corrects aberration of an ocular lens.

13. The optical system of claim 10, wherein the correction lens does not contribute to distortion, lateral chromatic aberration, astigmatism or field curvature.

14. The optical system of claim 10, wherein the first relay lens system is located between a second relay lens system and a third relay lens system.

15. The endoscope of claim 10, wherein only one correction lens group is used in the entire optical system.

16. Two or more relay lens systems for an optical system of an endoscope comprising:
    a first relay lens system comprising
       at least two rod lenses arranged in a series, each of the at least two rod lenses a singlet lens, and
       one doublet correction lens located between the at least two rod lenses and no other correction lens in the first relay lens system; and
    a plurality of additional relay lens pairs each having two symmetric singlet rod lenses arranged in a series, so that the number of additional relay lens pairs is greater than the number of relay lens systems that have a correction lens group.

17. The two or more relay lens systems of claim 16, wherein the first relay lens system is located between a second relay lens system and a third relay lens system.

18. The two or more relay lens systems of claim 16, wherein the correction lens corrects aberration of the two or more relay lens systems.

19. The two or more relay lens systems of claim 16, wherein the plurality of additional relay lens system does not have a correction lens group.

20. The two or more relay lens systems of claim 16, wherein only one correction lens group is used in the entire optical system.

* * * * *